(12) United States Patent
Hasan

(10) Patent No.: US 11,560,595 B2
(45) Date of Patent: Jan. 24, 2023

(54) METHOD FOR PREVENTING PROGRESSION TO TYPE II DIABETES

(71) Applicant: DASMAN DIABETES INSTITUTE, Dasman (KW)

(72) Inventor: Amal Ahmad Ali Hasan, Jabriya (KW)

(73) Assignee: DASMAN DIABETES INSTITUTE, Dasman (KW)

( * ) Notice: Subject to any disclaimer, the term of this patent is extended or adjusted under 35 U.S.C. 154(b) by 0 days.

(21) Appl. No.: 16/592,012

(22) Filed: Oct. 3, 2019

(65) Prior Publication Data

US 2021/0102252 A1    Apr. 8, 2021

(51) Int. Cl.
*C12Q 1/6883*    (2018.01)

(52) U.S. Cl.
CPC ..... *C12Q 1/6883* (2013.01); *C12Q 2600/106* (2013.01); *C12Q 2600/118* (2013.01); *C12Q 2600/158* (2013.01)

(58) Field of Classification Search
CPC ................................................ C12Q 2600/118
See application file for complete search history.

(56) References Cited

U.S. PATENT DOCUMENTS

| | | | |
|---|---|---|---|
| 8,147,817 B2 | 4/2012 | Lee | |
| 8,796,182 B2* | 8/2014 | Steinthorsdottir | ... C12Q 1/6883 435/6.1 |
| 9,840,545 B2 | 12/2017 | Sharma et al. | |
| 2005/0074805 A1 | 4/2005 | Kochan et al. | |
| 2016/0362487 A1 | 12/2016 | Murphy et al. | |

OTHER PUBLICATIONS

Zeyda et al., "Severe obesity increases adipose tissue expression of interleukin-33 and its receptor ST2, both predominantly detectable in endothelial cells of human adipose tissue", International Journal of Obesity, 2013, pp. 658-665 (Year: 2013).*
Lin et al. "Distribution and clinical association of plasma soluble ST2 during the development of type 2 diabetes", Diabetes Research and Clinical Practive, 2016, pp. 140-145 (Year: 2016).*
The American Diabetes Association, "Obesity Management for the Treatment of Type 2 Diabetes", Diabetes Care, 2016, pp. S47-S51 (Year: 2016).*
Barry et al., "Efficacy and effectiveness of screen and treat policies in prevention of type 2 diabetes: systematic review and meta-analysis of screening tests and interventions", BMJ, 2017, pp. 1-15 (Year: 2017).*
Armato et al., "Successful Treatment of Prediabetes in Clinical Practice: Targeting Insulin Resistance and b-Cell Dysfunction", Endocrine Practice, 2012, pp. 342-350 (Year: 2012).*
Slentz et al., "Effect of exercise training alone vs a combined exercise and nutritional lifestyle intervention on glucose homeostatsis in prediabetic individuals: a randomize controlled trial", Diabetologia, 2016, pp. 2088-2098 (Year: 2016).*
Yip et al. ("Weight Loss: Diet, Exercise, or Orlistat?" U.S. Pharmacist, Sep. 5-9, 2019, (Year: 2019).*
Hasan et al., "Association between Adipose Tissue Interleukin-33 and Immunometabolic Markers in Individuals with Varying Degrees of Glycemia", Disease Markers, Apr. 3, 2019, 16 pages (Year: 2019).*
Encyclopedia.com, "Spearman Rank Correlation Coefficient", obtained Dec. 30, 2020; https://www.encyclopedia.com/social-sciences/applied-and-social-sciences-magazines/spearman-rank-correlation-coefficient (Year: 2020).*
Vianello et al. "Dysfunctional EAT thickness may promote maladaptive heart remodeling in CVD patients through the ST2-IL33 system, directly related to EPAC protein expression", Scientific Reports, Jul. 17, 2019, 1-11 (Year: 2019).*
Mitchell, "Prebiotic supplementation with inulin and exercise influence gut microbiome composition and metabolic health", 2018, pp. 1-131 (Year: 2018).*
Ragusa et al. "Effects of obesity on IL-33/ST2 system in heart, adipose tissue and liver: study in the experimental model of Zucker rats", Experimental and Molecular Pathology, 2017, 354-359 (Year: 2017).*
Merriam-Webster, "Loss", https://www.merriam-webster.com/dictionary/loss; obtained Jul. 2, 2021 (Year: 2021).*
GoodRx, "You've Been Diagnosed With Prediabetes—What's Next?",https://www.goodrx.com/conditions/prediabetes/diagnosed-with-prediabetes-now-what; Jul. 2019 (Year: 2019).*
Mayo Clinic, "Diagnosis and treatment—Prediabetes", https://www.mayoclinic.org/diseases-conditions/prediabetes/diagnosis-treatment/drc-20355284?p=1, 2022 (Year: 2022).*
National Institute of Diabetes and Digestive and Kidney Diseases, "Preventing Type 2 Diabetes", https://www.niddk.nih.gov/health-information/diabetes/overview/preventing-type-2-diabetes, Dec. 2016 (Year: 2016).*
Fried et al. Type 2 Diabetes, Cardiovascular and Related Complications and Evidence-Based Complementary Treatments 2018, Available at https://www.google.com/books/edition/Type_2_Diabetes/F_p0DwAAQBAJ?hl=en&gbpv=1&dq=RT-PCR (Year: 2018).*
Diabetes: An Old Disease, a New Insight, Ed. Shamim Ahmad, Springer, 2013, p. 296 (Year: 2013).*

(Continued)

*Primary Examiner* — Lianko G Garyu
(74) *Attorney, Agent, or Firm* — Nath, Goldberg & Meyer; Richard C. Litman

(57) ABSTRACT

The method for preventing progression to Type II Diabetes includes determining whether a subject possesses a risk variant expression profile demonstrating dysregulation of the IL-33/ST2 axis, and providing an intervention to prevent progression to Type II Diabetes and/or to reverse prediabetes, including modifications of diet and exercise, administration of one or more pharmaceutical compounds, or a combination thereof. The method may be useful to reduce the risk of developing complications associated with Type II Diabetes or prediabetes, such as heart disease, stroke, or obesity. The pharmaceutical compound may be one or more pharmaceuticals capable of reducing circulating cholesterol, reducing blood glucose levels, reducing blood pressure, or a combination thereof.

9 Claims, 15 Drawing Sheets

(56) References Cited

OTHER PUBLICATIONS

Hostalek et al. "Therapeutic Use of Metformin in Prediabetes and Diabetes Prevention", Drugs, 2015, 1071-1094 (Year: 2015).*
Lowe, Metformin for Prediabetes: Is it Safe to Use?, https://khealth.com/learn/medication/metformin-for-prediabetes/, 2022 (Year: 2022).*
Lu et al., "Interleukin-33 prevents the development of autoimmune diabetes in NOD mice," Int'l Immunopharmacology, 70: pp. 9-15 (Feb. 18, 2019).
Hasan et al., "Association Between Adipose Tissue Interleukin-33 and Immunometabolic Markers in Individuals with Varying Degrees of Glycemia," Disease Markers, vol. 29, pp. 1-16 (Apr. 3, 2019).
Miller et al., "Interleukin-33 induces protective effects in adipose tissue inflammation during obesity in mice," Circulation Research, (107)5: pp. 650-658 (2010).
Miller and Liew, "The IL-33/ST2 pathway—a new therapeutic target in cardiovascular disease," Pharmacology & Therapeutics, 131(2): pp. 179-186(2011).
Miller et al., "IL-33 reduces the development of atherosclerosis," The Journal of Experimental Medicine, 205(2): pp. 339-346 (2008).
Hasan et al., "IL-33 is negatively associated with the BMI and confers a protective lipid/metabolic profile in non-diabetic but not diabetic subjects," BMC Immunology, 15(19): p. 1-9 (2014).
Brestoff et al., "Group 2 innate lymphoid cells promote beiging of white adipose tissue and limit obesity," Nature, 519(7542): pp. 242-246 (2015).
Lee et al., "Activated type 2 innate lymphoid cells regulate beige fat biogenesis," Cell, 160(0): pp. 74-87 (2015).

\* cited by examiner

METHOD FOR PREVENTING PROGRESSION TO TYPE II DIABETES

BACKGROUND

1. Field

The disclosure of the present patent application relates to the medical sciences, and particularly to a method for identifying subjects with prediabetes and intervening to prevent progression to Type II Diabetes and/or to reverse prediabetes.

2. Description of the Related Art

More than 3 million Americans are treated for Type II Diabetes every year. Type II Diabetes is a condition characterized by the failure of the body to make or use insulin correctly. This results in a dysregulation of glucose metabolism, resulting in increased blood glucose levels. If untreated, Type II Diabetes can lead to hyperglycemia, diabetic ketoacidosis, and death. Diagnosis of Type II Diabetes can be complicated, as the development of diabetes is not always accompanied by clear symptoms. Even when the symptoms are clear, they frequently include minor symptoms such as increased thirst and urination, fatigue, weight loss, or slow healing of cuts or sores. These symptoms may not be severe enough to cause a subject to seek medical attention. Thus, there is a need to develop better methods of diagnosing Type II Diabetes.

Prediabetes is a condition characterized by an increased blood sugar level above normal, but without having increased sufficiently to be classified as Type II Diabetes. Prediabetes often progresses to Type II Diabetes, absent appropriate intervention.

Thus, a method for identifying subjects with prediabetes and predicting and preventing progression to Type II Diabetes solving the aforementioned problems is desired.

SUMMARY

The present subject matter relates to a method for preventing progression to Type II Diabetes, including detecting increased risk of developing Type II Diabetes in a subject and intervening to prevent development of Type II Diabetes and/or to reverse prediabetes. In an embodiment, the intervention may include administering a pharmaceutical composition to the subject, administering a dietary supplement to the subject, prescribing a modified diet or exercise regime for the subject, or a combination thereof. In an embodiment, a subject's risk of developing Type II Diabetes may be determined by identifying dysfunction in a subject's IL-33/ST2 expression profile in adipose tissues. In an embodiment, the subject is identified as being at risk of developing Type II Diabetes if the expression levels of IL-33 and ST2 in the subject's adipose tissue are not directly correlated to one another. In an alternative embodiment, the optimal relative gene expression of IL-33 is ≥1.5. This relative gene expression level can be based on measurements from adipose tissue of the subject.

In an embodiment, the subject may be of Arab descent.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
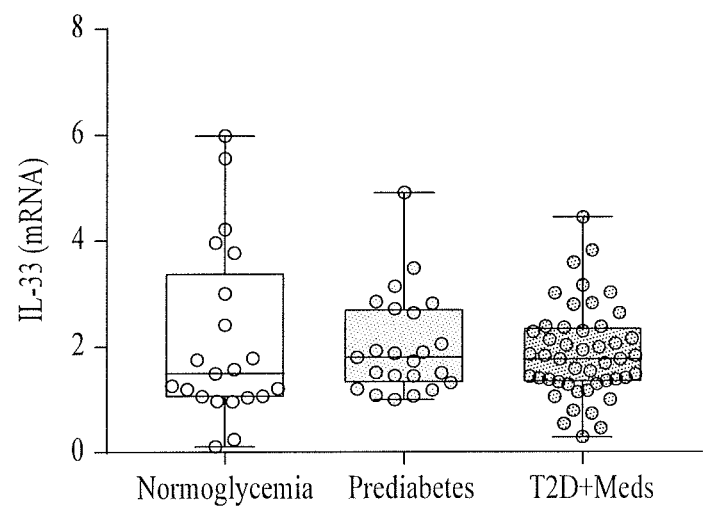
FIG. 1A depicts a box plot of expression of IL-33 in adipose tissue of subjects having normoglycemia, prediabetes, and managed Type II Diabetes.

The present subject matter relates to a method for preventing progression to Type II Diabetes, including detecting increased risk of developing Type II Diabetes in a subject and intervening to prevent development of Type II Diabetes. In an embodiment, the intervention may include administering a pharmaceutical composition to the subject, administering a dietary supplement to the subject, prescribing a modified diet or exercise regime for the subject, or a combination thereof. In an embodiment, a subject's risk of developing type II diabetes may be determined by identifying dysfunction in a subject's IL-33/ST2 expression profile. In an embodiment, the subject is identified as being at risk of developing Type II Diabetes if the expression of IL-33 and ST2 is not directly correlated. In another embodiment, the expression profile is determined from the subject's adipose tissue. In an alternative embodiment, the optimal relative gene expression of IL-33 is $\geq 1.5$. This relative gene expression level can be based on measurements from adipose tissue of the subject.

As used herein, the term "about" when used to modify a numeral, means within 10% of the numeral's value.

As used herein, "Type II Diabetes" is a collection of health risks and conditions that may increase the chance of developing, and relate to, heart disease, stroke, and diabetes. These health risks and conditions include increased blood pressure, high blood sugar, excess body fat, particularly excess body fat around the waist, abnormal cholesterol or triglyceride levels, non-alcoholic steatohepatitis, and microvascular and macrovascular complications including but not limited to neuropathy, nephropathy, and retinopathy. In order to be diagnosed with Type II Diabetes, a subject must generally exceed specific parameters for three or more of the health risks and conditions. Generally, Type H Diabetes is characterized by test results in subjects not taking a glucose-lowering medication indicating at least one of: a fasting blood sugar $\geq 126$ mg/dL, an HbA1C$\geq 6.5$, and/or an oral glucose tolerance test result above 200 mg/dL.

As used herein, "prediabetes" is a health condition characterized by a blood sugar and/or HbA1c level that is higher than normal, but not yet high enough to support a diagnosis of Diabetes. Generally, prediabetes is characterized by a fasting blood sugar ranging from 100-125 mg/dL and/or an HbA1c between 5.7% and 6.4%, in subjects not taking a glucose-lowering medication.

As used herein, "normoglycemia" refers to a health condition characterized by a normal blood sugar and/or HbA1c level. Generally, normoglycemia is characterized by a fasting blood sugar of <100 mg/dL and/or an HbA1c<5.7%, in subjects not taking a glucose lowering medication.

As used herein, "nucleic acid" means a polynucleotide such as a single or double-stranded DNA or RNA molecule, including, for example, genomic DNA, cDNA, and mRNA. The term nucleic acid includes nucleic acid molecules of both natural and synthetic origin, as well as molecules of linear, circular, or branched configuration representing either sense or antisense strands, or both, of a native nucleic acid molecule.

As used herein, "subject" means a mammal, such as a human being.

As used herein, "biological sample" means any biological material from which nucleic acid molecules can be prepared. Non-limiting examples of suitable biological samples useful herein include whole blood, plasma, saliva, cheek swab, or other bodily fluids, cells or tissues that contain nucleic acids.

As used herein, "adipose tissue" means loose connective tissue composed of fat cells, or adipocytes. Adipose tissue mainly acts as a source of energy storage, and thus plays a central role in diseases relating to metabolism, such as Type II Diabetes. Adipose tissue is primarily found just beneath the skin, but also surrounds the internal organs.

As used herein, "risk variant" corresponds to variations in the expression profile of a subject's genes which are correlated with an increased risk of developing Type II Diabetes.

As used herein, "probiotic" means any live bacteria which, upon consumption by a subject, may colonize the subject's large intestine and/or change the microbiome of the subject's oral cavity.

As used herein, "prebiotic" means any food or dietary supplement which, upon consumption by a subject, may induce the growth or activity of beneficial microorganisms in the subject's gut.

As used herein, "synbiotic" means any synergistic combination of one or more probiotics with one or more prebiotics.

Many methods are available for detection of one or more risk variants, including sequencing methods, re-sequencing methods, amplification methods, and hybridization methods. Analysis of nucleic acids in a biological sample from an individual, whether amplified or not, may be performed using any of these methods. Exemplary methods include but are not limited to polymerase chain reaction (PCR), reverse-transcription PCR (RT-PCR), TAQMAN Gene Expression assays, and molecular beacon assays. One of ordinary skill in the art would understand that any known method of amplification of a nucleotide sequence could be incorporated into a method to detect one or more risk variant expression profiles. One of ordinary skill in the art would further understand that these methods of amplification of a nucleotide sequence could use RNA, or a combination of RNA and DNA.

These assays may be multiplexed, meaning two or more reactions may be conducted simultaneously in the same physical location, such as in the same tube or on the same substrate, such as a biochip, ensuring that the reaction products of the multiplexed reactions can be distinguished. For example, TAQMAN or molecular beacon assays can be multiplexed by use of monitoring of accumulation or depletion of two different fluorochromes corresponding to different sequence specific probes.

As used herein, "PCR" is any method involving the amplification of a nucleotide sequence based upon complementary primer binding to a target sequence. One of ordinary skill in the art will understand that PCR may be employed as part of many techniques for identifying a risk variant gene expression profile.

As used herein, "RT-PCR" is any method involving the amplification of a RNA sequence using a reverse transcriptase to produce a cDNA sequence, followed by amplification of a nucleotide sequence based upon complementary primer binding to a target sequence. One of ordinary skill in the art will understand that RT-PCR may be employed as part of many techniques for identifying a risk variant gene expression profile.

As used herein, a "TAQMAN Gene Expression assay" is any method using a target allele specific probe bearing a 5' fluorescent dye label. In general, when the allele specific probe is used to amplify the target sequence, the 5'-nuclease activity of the polymerase cleaves the 5' fluorescent dye label off of the probe, changing the molecular weight of the fluorescent dye molecule and therefore changing the fluorescence polarization. This change in fluorescence polarization may be detected, thereby confirming the presence of the target allele.

When implementing methods for detection of one or more risk variant expression profiles, an array may be used to perform a high-throughput assay. The array generally comprises one or more reagents, such as nucleic acid primers and/or probes, for identifying in a nucleic acid sample from a subject the occurrence of a variant expression profile of one or more genes. These reagents may be immobilized onto a substrate in a spatially addressable manner, such that each reagent is located at a different, identifiable, position on the array. The substrate may include multi-welled plates, ceramic chips, or beads. In a non-limiting example, the substrate may be a 96 well dish, with each well constituting a reaction chamber within which separate reactions comprising identified constituents may be performed. The reaction constituents may include primers for amplifying RNA or DNA, or probes for binding specific sequences and reaction reagents. The reagents may be in any suitable form, including but not limited to: in solution, dried, lyophilized, or glassified. In a further non-limiting example, the array may include two or more sets of beads, with each bead having an identifiable marker, such as a quantum dot or fluorescent tag, so that the beads may be individually identified using, for example, a flow cytometer. Non-limiting examples of array technologies that may be employed include: the Affymetrix GeneChip® Array or the GenChip® CustomSeq® Resequencing Arrays. Informatics and/or statistical software or other computer-implemented processes for analyzing array data and/or identifying genetic risk factors from data obtained from a patient sample are well known in the art and would be readily understood by the ordinarily skilled artisan.

Other methods useful for determining the presence or absence of a variant gene expression profile now known in the art or later developed may also be used when performing the method for preventing progression to Type II Diabetes.

In an embodiment, the subject may be of Arab descent.

In an embodiment, the method for preventing progression to Type II Diabetes may include identifying a subject possessing a risk variant expression profile. The risk variant expression profile may include a dysfunction in the subject's IL-33/ST2 expression profile. The dysfunction may be a loss of direct correlation between the expression levels of IL-33 and ST2 in a subject. The loss in correlation between the expression levels of IL-33 and ST2 in the subject may be observable in adipose tissues, in tests of blood plasma or serum, or in tests of peripheral blood mononuclear cells (PBMCs).

In an alternative embodiment, the risk variant expression profile may include a dysfunction in the subject's IL-33/FGL2 expression profile. The dysfunction may be a loss of direct correlation between the expression levels of IL-33 and FGL2 in a subject.

In an alternative embodiment, the risk variant expression profile may include a dysfunction in the subject's IL-33/PRDM16 expression profile. The dysfunction may be a loss of direct correlation between the expression levels of IL-33 and PRDM16 in the subject.

In an alternative embodiment, the risk variant expression profile may include a dysfunction in the subject's IL-33/CD302 expression profile. The dysfunction may be a loss of direct correlation between the expression levels of IL-33 and CD302 in the subject.

In an alternative embodiment, the risk variant expression profile may include a dysfunction in the subject's IL-33/TLR9 expression profile. The dysfunction may be the presence of a direct correlation between the expression levels of IL-33 and TLR9 in the subject.

In an alternative embodiment, the risk variant expression profile may include a dysfunction in the subject's IL-33/CCL7 expression profile. The dysfunction may be a loss of inverse correlation between the expression levels of IL-33 and CCL7 in the subject.

In an alternative embodiment, the risk variant expression profile may include a dysfunction in the subject's IL-33/IL-6 expression profile, if the subject has elevated IL-33 levels. The dysfunction may be a loss of association between the expression levels of IL-33 and IL-6 in the subject.

In an embodiment, the risk variant expression profile may be determined by collecting a biological sample from a subject and detecting the expression levels of one or more genes in the biological sample using PCR, RT-PCR, TAQMAN Gene Expression Assays, molecular beacon assays, or the like.

In an embodiment, the biological sample may be a sample of the subject's adipose tissue. A biological sample comprising adipose tissue may be collected by any known technique. In a non-limiting example, biological samples of adipose tissue may be collected by surgical biopsy or by fine needle biopsy. These biopsy procedures may be used to collect adipose tissue samples from adipose tissues that are subcutaneous.

In an embodiment, a subject identified as possessing a risk variant expression profile may then receive one or more interventions to prevent progression to Type II Diabetes. Possible interventions include but are not limited to pharmaceutical treatments, diet, exercise, consumption of one or more dietary supplements, or a combination thereof. In a non-limiting example, a subject found to possess the risk variant expression profile, and thus to be at increased risk of developing Type II Diabetes, may be prescribed at least 30 minutes of exercise a day, or a diet that is low in fat and refined, processed sugars, or a combination thereof. In a further non-limiting example a subject found to be at increased risk of developing Type II Diabetes may be prescribed any appropriate dietary restriction, including but not limited to restricted calorie, low fat, low carbohydrate, flexitarian, vegan, high fiber, and raw food diets. In some embodiments, the subject may receive intervention via a dietary supplement in addition to the dietary restriction.

In a further non-limiting example, a subject found to possess the risk variant expression profile, and thus to be at increased risk of developing Type II Diabetes, may receive intervention via a dietary supplement. The dietary supplement may include a probiotic, a prebiotic, a symbiotic, or a combination thereof.

In a further non-limiting example, a subject found to possess the risk variant expression profile, and thus to be at increased risk of developing Type II Diabetes, may receive intervention via a pharmaceutical treatment. Potential pharmaceuticals for administration to a subject at increased risk of developing Type II Diabetes include compositions capable of reducing cholesterol/triglycerides, compositions capable of reducing blood glucose levels, and compositions capable of reducing blood pressure, including but not limited to atorvastatin, fluvastatin, lovastatin, pitavastatin, pravastatin, rosuvastatin calcium, simvastatin, metformin, sulfonylureas, meglitinides, thiazolinediones, DPP-4 inhibitors, GLP-1 receptor agonists, SGLT2 inhibitors, insulin, diuretics, beta-blockers, ACE inhibitors, angiotensin II receptor blockers, calcium channel blockers, alpha blockers, alpha-2 receptor agonists, non-steroidal anti-inflammatory drugs, pharmaceutical grade probiotics, or a combination thereof.

In an embodiment, intervention to prevent the progression to Type II Diabetes may also be used to prevent the development of one or more comorbidities associated with Type II Diabetes, including but not limited to hypertension, obesity, nonalcoholic steatohepatitis, and cardiovascular disease.

In a further embodiment, the intervention may be effective in reversing prediabetes in the subject, in addition to preventing progression to Type II Diabetes in the subject. In this regard, one or more of the treatments described herein may attack and reverse the lack of correlation between IL-33 and ST2 in patients with prediabetes, thereby reversing the prediabetes and preventing the progression to Type II Diabetes. In an alternative embodiment, one or more of the treatments described herein may restore the correlation between IL-33 and ST2.

A kit used to carry out the method for preventing progression to Type II Diabetes may contain various components needed for carrying out the method packaged in separate containers and/or vials and including instructions for carrying out the method. In a non-limiting example, some or all of the various components and other ingredients needed to detect the presence of the risk variant expression profile, such as buffers, primers, enzymes, control samples or standards and the like can be packaged separately but provided for use in the same container. Instructions for carrying out the method can be included inside the container, as a separate insert, or as a label on the container and/or on the separate packaging. The kit may also contain the necessary software (or instructions to download the same) needed to interpret the results obtained with the kit, or for utilizing the results in a particular high-throughput assay selected for carrying out the method.

In an embodiment, the kit may include primers for the amplification and/or quantification of IL-33 and/or ST2 expression. In this embodiment, the kit may also include reagents sufficient to perform one or more methods of detection of a risk variant expression profile.

The following examples illustrate the present teachings.

Example 1

Association Between Adipose Tissue IL-33 and Immunometabolic Markers

1. Study Participants.

The following examples report the results of a study conducted on 91 adults between the ages of 23 and 72. All subjects provided written informed consent to participate in the study. Subjects were classified based upon HbA1c (according to criteria established by the American Diabetes Association) into the normoglycemia group (HbA1c<5.7%), prediabetes (HbA1c between 5.7% and 6.4%; not currently taking glucose-lowering medications), and type IT diabetics (diagnosis of Type II Diabetes and HbA1c≥6.5%; or taking any type of glucose-lowering medication). Commonly observed comorbid health conditions of subjects with Type II Diabetes included hypertension, dyslipidemia, cardiovascular disease, kidney disease, and neuropathy.

2. Anthropometric and Biochemical Measurements.

Anthropometric and biochemical data was collected for each subject, including height (m) and weight (kg); which were then used to calculate BMI (Weight/Height$^2$). BMI was then used as an overall index of adiposity. Waist to hip ratios were also calculated, and whole-body metrics including percentage of body fat (PBF), soft lean mass (SLM), and total body water (TBW) were measured using an IOI 353 Body Composition Analyzer (Jawon Medical). Fasting blood samples were obtained and plasma glucose, serum total cholesterol, triglycerides (TG), and high-density lipoprotein (HDL) cholesterol were measured using a Siemens Dimension RXL chemistry analyzer (Diamond Diagnostics, Holliston, Mass.). Low-density lipoprotein (LDL) cholesterol was also estimated. Glycated hemoglobin (HbA1c) was determined using the Bio-Rad Variant program (Hercules, Calif.). High-sensitivity C-reactive protein (hsCRP) was measured using ELISA kits (Bio-Vendor, USA). Optimal values for TG (<1.7 mmol/L), total cholesterol (<5.2 mmol/L), LDL cholesterol (<3.3 mmol/L), and HDL cholesterol (>1.03 mmol/L) were based on the American Heart Association's guidelines. The resulting anthropometric and biochemical data are summarized in Table 1.

TABLE 1

Anthropometric and biochemical characteristics of the study groups

| Participants | Normoglycemia | Prediabetes | Type II Diabetes | P value* |
|---|---|---|---|---|
| Total number (n) | 21 | 23 | 47 | — |
| Age (years) | 39 ± 11 | 46 ± 12.1 | 54 (23, 72) | <0.0001 |
| Body mass index (kg/m$^2$) | 30.1 ± 5.2 | 31.16 ± 5.54 | 31.3 ± 3.79 | 0.38 |
| Percentage body fat (%) | 34.4 ± 6.5 (n = 20) | 34.92 ± 6.7 (n = 18) | 35.44 ± 5.59 (n = 37) | 0.85 |
| Soft lean mass (%) | 59.97 ± 6.41 (n = 20) | 59.45 ± 6.68 (n = 18) | 58.96 ± 5.58 (n = 37) | 0.85 |
| Total body water (%) | 47.25 ± 4.65 (n = 20) | 46.88 ± 4.87 (n = 18) | 46.53 ± 4.05 (n = 37) | 0.87 |
| SLM to PBF ratio | 1.64 (1.1, 3.7) (n = 20) | 1.8 ± 0.6 (n = 18) | 1.58 (1.07, 3.19) (n = 37) | 0.85 |
| Waist to Hip Ratio | 0.88 (0.48, 1.07) (n = 20) | 0.91 ± 0.12 (n = 19) | 0.94 (0.77, 2.34) (n = 37) | 0.12 |
| Fasting Glucose (mmol/L) | 5.1 ± 0.38 | 5.3 ± 0.54 | 8.2 (4.6, 17.7) | <0.0001 |
| HbA1c (%) | 5.3 (4.4, 5.6) (n = 20) | 5.87 ± 0.14 | 8.2 ± 1.65 (4.9, 12.3) | <0.0001 |
| Total Cholesterol (mmol/L) | 4.7 ± 0.8 | 5.4 ± 0.88 | 4.63 (2.5, 8.5) (n = 46) | 0.038 |
| HDL Cholesterol (mmol/L) | 1.16 (0.88, 2.24) | 1.29 ± 0.3 | 1.16 ± 0.3 (n = 45) | 0.18 |
| LDL Cholesterol (mmol/L) | 2.99 ± 0.66 | 3.62 ± 0.75 | 2.8 ± 1.16 (n = 44) | 0.003 |
| Triglyceride (mmol/L) | 0.79 (0.43, 2.93) | 1.1 ± 0.44 | 1.39 (0.36, 7.63) (n = 46) | 0.0009 |
| hsCRP (µg/mL) | 4.48 ± 3.24 (n = 12) | 3.85 (0.72, 8.14) (n = 16) | 4.72 (0.94, 17.92) (n = 27) | 0.4 |
| White blood cell count (10$^9$/L) | 5.7 ± 1.35 | 6.8 ± 2.17 (n = 21) | 7.4 ± 2.1 (n = 45) | 0.006 |

Data shown represent either the standard deviation or the mean or the median (min, max) as indicated.
*Nonparametric Kruskal-Wallis test of the medians.

3. Collection of Subcutaneous Adipose Tissue Samples.

Human adipose tissues (about 0.5 g) were collected from each subject using routine surgical procedures from the abdominal subcutaneous fat pads situated lateral to the umbilicus. Briefly, the periumbilical area was sterilized using alcohol swabs and then locally anesthetized using 2% lidocaine (2 mL). A small superficial skin incision (0.5 cm) was then made; after which, fat tissue was collected using punch biopsy. Freshly collected adipose tissues (about 50 mg to about 100 mg) were preserved in RNAlater or embedded in optimal cutting temperature (OCT) compound and stored at −80° C. until use.

4. RNA Isolation from Adipose Tissue Samples.

Total cellular RNA was purified using the RNeasy kit (Qiagen, Valencia, Calif., USA) as per the manufacturer's instructions. Briefly, adipose tissue samples (preserved in RNAlater or embedded in OCT) were thawed and homogenized in Qiazol lysis solution using a TissueRuptor (Qiagen, Hilden, Germany) at 33,000 rpm for 40 s. The homogenates were then treated with chloroform and separated into aqueous and organic phases by centrifugations at 12,000×g for 15 min at 4° C. After the upper aqueous RNA phase was collected, 70% ethanol was then added. Thereafter, the sample was applied to an RNeasy spin column to allow total RNA binding with the membrane and to wash out phenol and other contaminants. High-quality RNA was then eluted in RNase-free water. The quantity and quality of the isolated RNA were determined using an Epoch™ Spectrophotometer System (BioTek, Winooski, Vt., USA) and formaldehyde-agarose gel electrophoresis, respectively.

5. Real-Time Reverse Transcription-Polymerase Chain Reaction.

Real-time reverse transcription-polymerase chain reaction (RT-PCR) was conducted, according to protocols known to those of ordinary skill in the art. Briefly, RNA samples (1 µg each) were reverse transcribed to cDNA using random hexamer primers and TaqMan reverse transcription reagents (High-Capacity cDNA Reverse Transcription kit; Applied Biosystems, CA, USA). For RT-PCR, cDNA (50 ng) was amplified using TaqMan Gene Expression MasterMix (Applied Biosystems, CA, USA) and gene-specific 20× TaqMan Gene Expression Assays (Applied Biosystems, CA, USA) containing forward and reverse primers and a target specific TaqMan minor groove binder (MGB) probe labeled with 6-fluorescein amidite dye at the 5' end and a nonfluorescent quencher MGB at the 3' end of the probe for 40 cycles of PCR reaction using a 7500 Fast Real-Time PCR System (Applied Biosystems, CA, USA). Each cycle consisted of a denaturation phase for 15 s at 95° C. and an annealing/extension phase for 1 min at 60° C. The cycle was started after uracil DNA glycosylase activation (50° C. for 2 min) and AmpliTaq Gold enzyme activation (95° C. for 10 min). Amplified glyceraldehyde 3-phosphate dehydrogenase (GAPDII) expression was used as an internal control to normalize differences between individual samples. The comparative $C_T$ method was used to analyze the relative gene expression of various mediators using the formula $2^{-\Delta\Delta C_T}$ whereby $\Delta\Delta C_T=[C_T$ gene of interest$-C_T$ endogenous control; $\Delta C_T$]–normal weight control with highest $\Delta C_T$. In this regard, the relative mRNA fold expression for each specific gene was calculated by first normalizing the $C_T$ values to an endogenous control (GAPDH) ($\Delta C_T$) and then normalizing the $\Delta C_T$ of each gene expression to the highest $\Delta C_T$ of the normal weight control.

6. Statistical Methods.

The GraphPad Prism software (version 7.04; San Diego, Calif., USA) was used for all statistical analyses. Correlation analysis was conducted using nonparametric Spearman's r test, and results were validated using an extra test wherein an estimated cutoff value for IL-33 (median mRNA expression of IL-33 in individuals with normoglycemia=1.5) was used to compare between low and high IL-33 in terms of the medians of various biomarkers. To compare between two groups of data, the nonparametric Mann-Whitney test was utilized with a P value of less than 0.05 being considered statistically significant.

7. Adipose Tissue IL-33 and its Association with ST2.

Figure 1B:
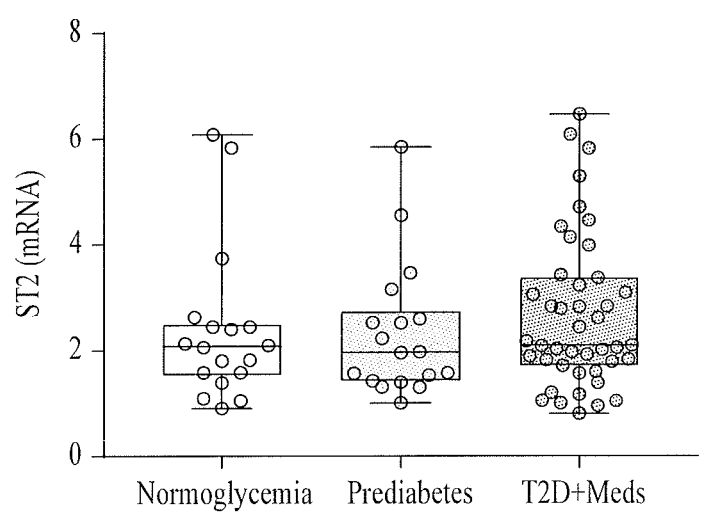
FIG. 1B depicts a box plot of expression of ST2 in adipose tissue of subjects having normoglycemia, prediabetes, and managed Type II Diabetes.
Figure 1C:
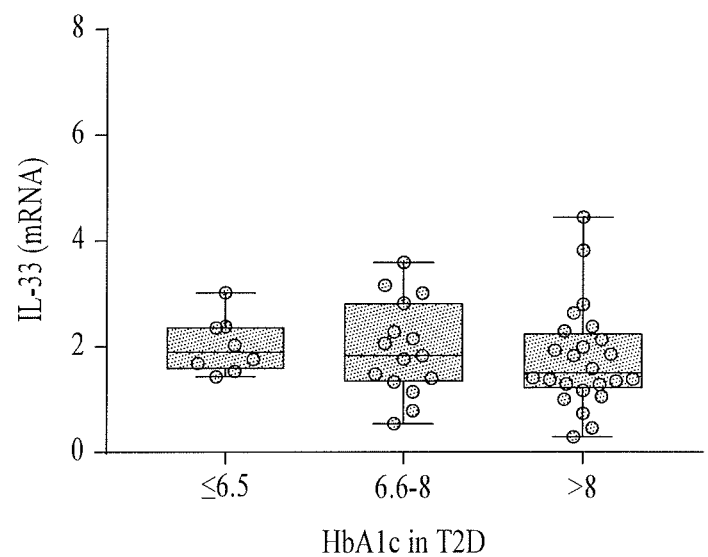
FIG. 1C depicts a box plot of expression of IL-33 in adipose tissue of subjects having varying HbA1c levels.
Figure 1D:
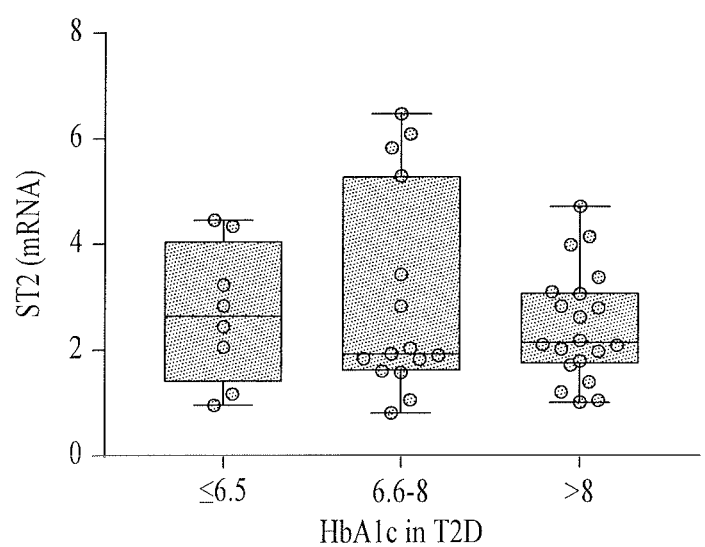
FIG. 1D depicts a box plot of expression of ST2 in adipose tissue of subjects having varying HbA1c levels.
Figure 2A:
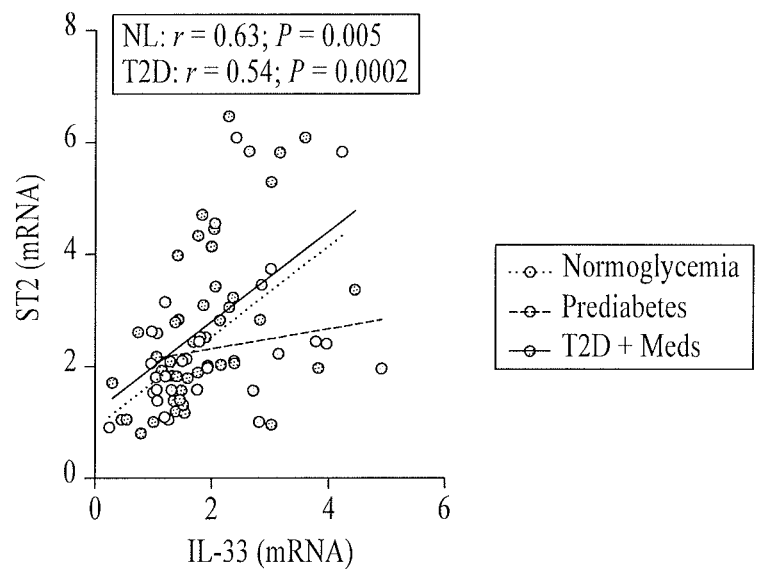
FIG. 2A depicts a scatter plot of the association between IL-33 expression levels and ST2 expression levels in adipose tissue of subjects having normoglycemia, prediabetes, and managed Type II Diabetes.
Figure 2B:
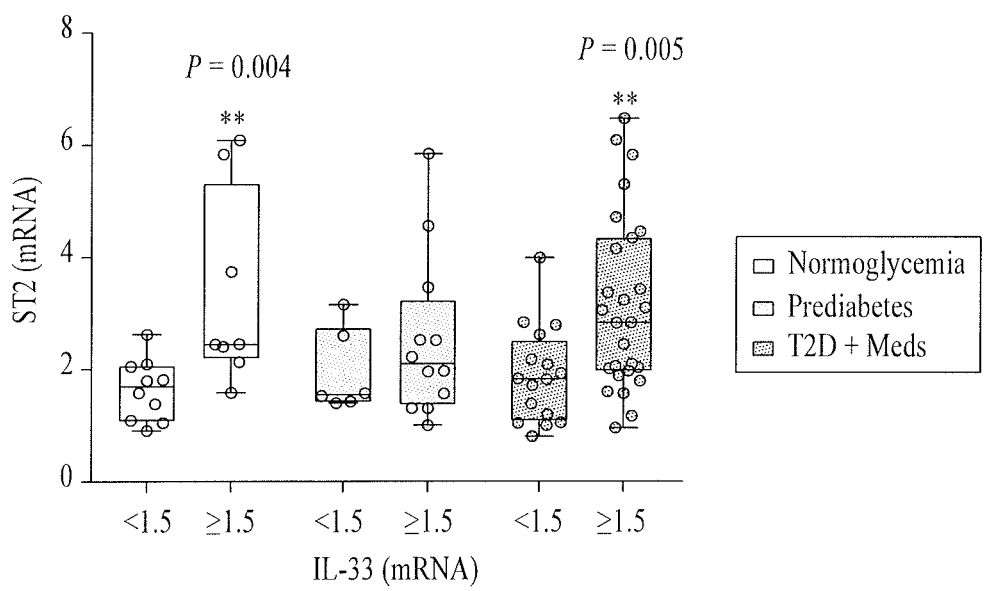
FIG. 2B depicts a box plot of the association between IL-33 expression levels and ST2 expression levels in adipose tissue of subjects having normoglycemia, prediabetes, and managed Type II Diabetes.

No difference was observed in the expression levels of IL-33 or ST2 among individuals with normoglycemia, prediabetes, or Type II Diabetes (see FIGS. 1A-1B). In addition, no difference was observed in the expression levels of IL-33 or ST2 among individuals with Type II Diabetes who had varying degrees of glycemic control (HbA1c≤6.5, HbA1c=6.6-8.0, HbA1c>8.0) (see FIGS. 1C-1D). IL-33 was directly correlated with ST2 in individuals with normoglycemia (r=0.63; P=0.005; n=18) and Type II Diabetes (r=0.54; P=0.0002; n=43) but not in those with prediabetes. Similarly, higher levels of IL-33 were associated with significantly higher ST2 in individuals with normoglycemia (P=0.004; median 2.83, n=27 vs. median 1.83, n=16) but not in those with prediabetes (see FIGS. 2A-2B).

8. Association Between Adipose Tissue IL-33 and Clinicometabolic Parameters.

Figure 3A:
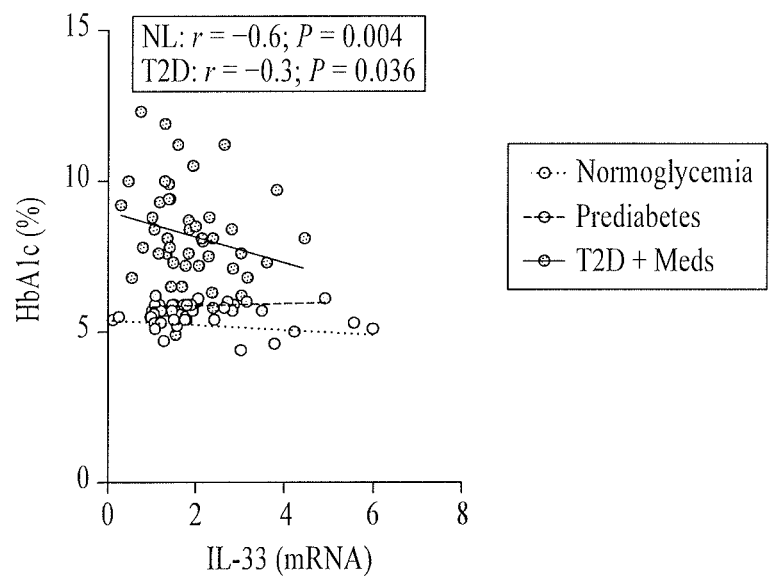
FIG. 3A depicts a scatter plot of the association between IL-33 expression levels and HbA1c levels in subjects having normoglycemia, prediabetes, and managed Type II Diabetes.
Figure 3B:
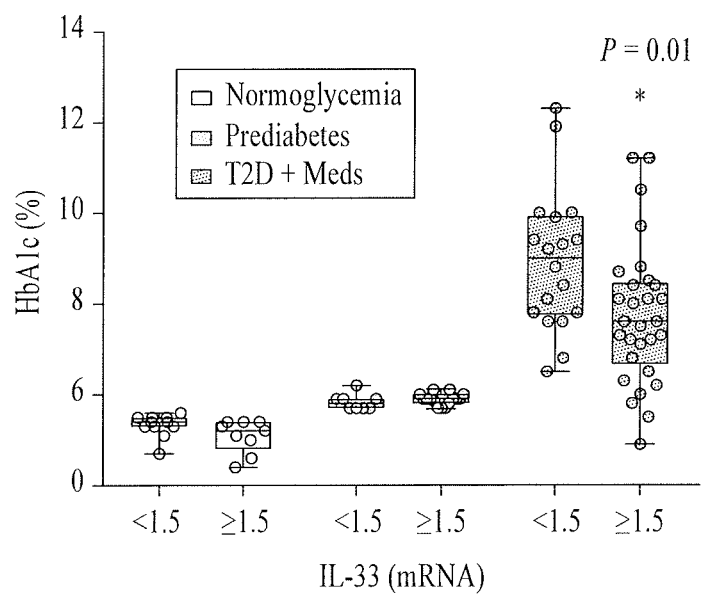
FIG. 3B depicts a box plot of the association between IL-33 expression levels and HbA1c levels in subjects having normoglycemia, prediabetes, and managed Type II Diabetes.
Figure 3C:
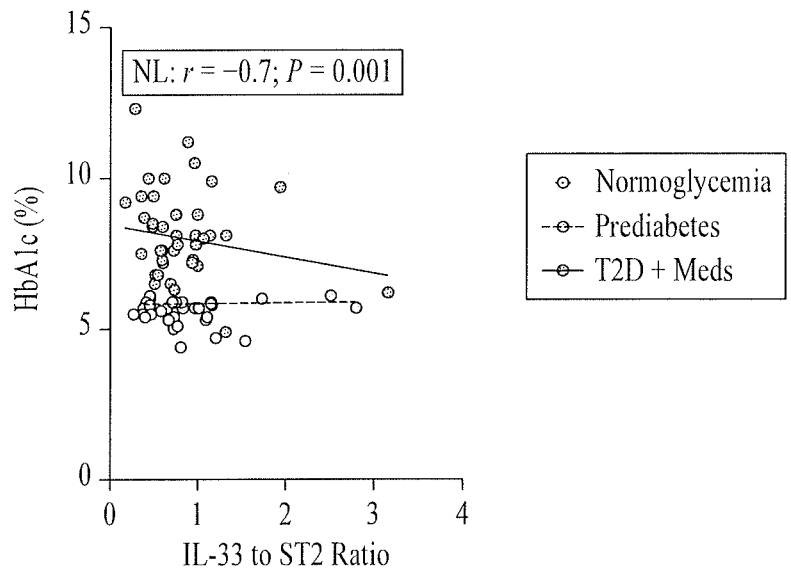
FIG. 3C depicts a scatter plot of the association between the IL-33 to ST2 expression ratio and HbA1c levels in subjects having normoglycemia, prediabetes, and managed Type II Diabetes.

IL-33 was inversely correlated with HbA1c in individuals with normoglycemia (r=−0.6; P=0.004; n=20) and Type II Diabetes (r=−0.3; P=0.036; n=47) but not in those with prediabetes. Among individuals with normoglycemia, those who had higher levels of IL-33 had lower (although statistically nonsignificant) HbA1c compared with those who had lower levels of IL-33 (P=0.07; median 5.2, n=9 vs. median 5.4, n=11). This pattern was not observed among individuals with prediabetes. Among individuals with Type II Diabetes, those who had higher levels of IL-33 had significantly lower HbA1c compared with those who had lower levels of IL-33 (P=0.01; median 7.6, n=29 vs. median 9, n=18) (see FIGS. 3A-3B). No correlation was observed between ST2 and HbA1c among individuals with normoglycemia, prediabetes, or Type II Diabetes. The ratio of IL-33 to ST2 was inversely correlated with HbA1c in individuals with normoglycemia (r=−0.7; P=0.001; n=17) but not in those with prediabetes or Type II Diabetes (See FIG. 3C).

Figure 3D:
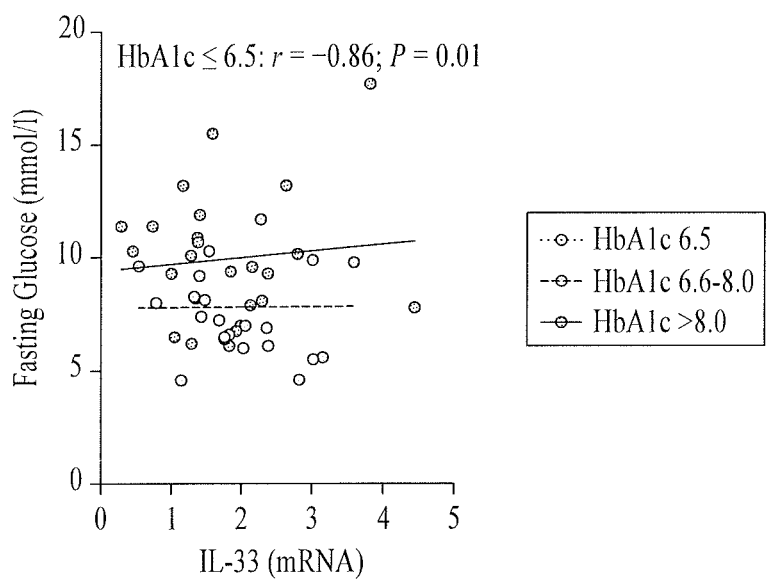
FIG. 3D depicts a scatter plot of the association between the IL-33 expression levels and fasting glucose levels in subjects having managed Type II Diabetes with different ranges of HbA1c.
Figure 4A:
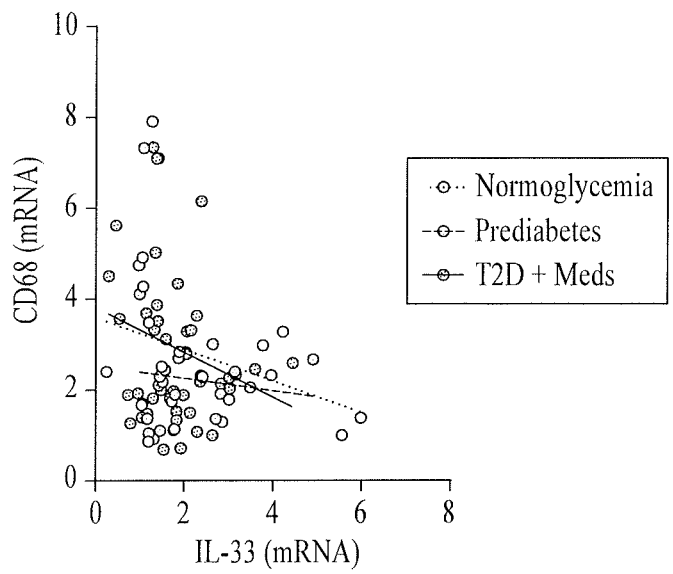
FIG. 4A depicts a scatter plot of the association between the adipose tissue IL-33 expression levels and CD68 expression levels in subjects having normoglycemia, prediabetes, and managed Type II Diabetes.
Figure 4B:
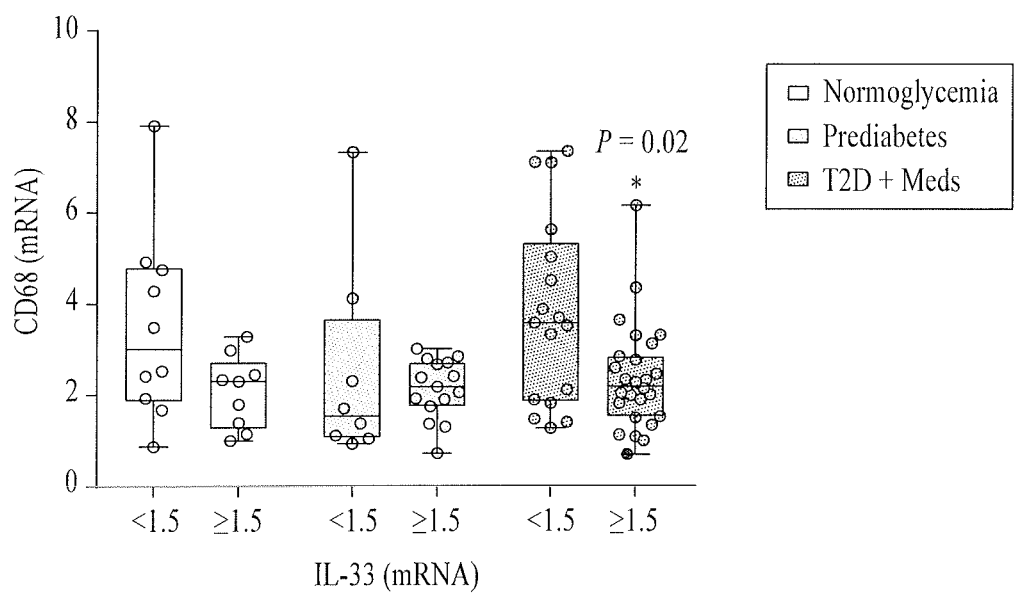
FIG. 4B depicts a box plot of the association between the adipose tissue IL-33 expression levels and CD68 expression levels in subjects having normoglycemia, prediabetes, and managed Type II Diabetes.

To determine whether the inverse correlation between IL-33 and HbA1c in people with Type II Diabetes was confined to individuals with a better glycemic control, they were divided into three groups based on their level of glycemic control (i.e., HbA1c≤6.5, HvA1c 6.6-8.0, and HbA1c>8.0) and analyzed separately. Accordingly, IL-33 was not correlated with HbA1c in subjects with Type II Diabetes when stratified for the subjects' level of glycemic control. However, IL-33 was inversely correlated with fasting glucose (r=−0.86; P=0.01) in subjects with Type II Diabetes who had a better glycemic control (HbA1c≤6.5; n=8) (see FIG. 3D). No correlation was found between adipose tissue IL-33 and circulating lipids (total cholesterol, LDL, HDL, and TG), BMI, body composition (PBF, SLM %, and TBW %), or waist to hip ratio among subjects with normoglycemia, prediabetes, or Type II Diabetes. There was no correlation between IL-33 and CD68 (a universal macrophage marker); however, comparative analysis revealed that higher levels of IL-33 were associated with significantly lower CD68 (P=0.02; median 2.19, n=27 vs. median 3.57, 71=17) in individuals with Type II Diabetes (see FIGS. 4A-4B). There was no correlation between IL-33 and CD11c, CD68, CD163, and chemokine receptors CCR1, CCR2, and CCR5 (data not shown). With regard to PRRs, IL-33 was directly correlated with the C-type lectin receptor CD302 in individuals with normoglycemia (r=0.54; P=0.01; n=21) and Type II Diabetes (r=0.41; P=0.004; n=47) but not in those with prediabetes.

Figure 4C:
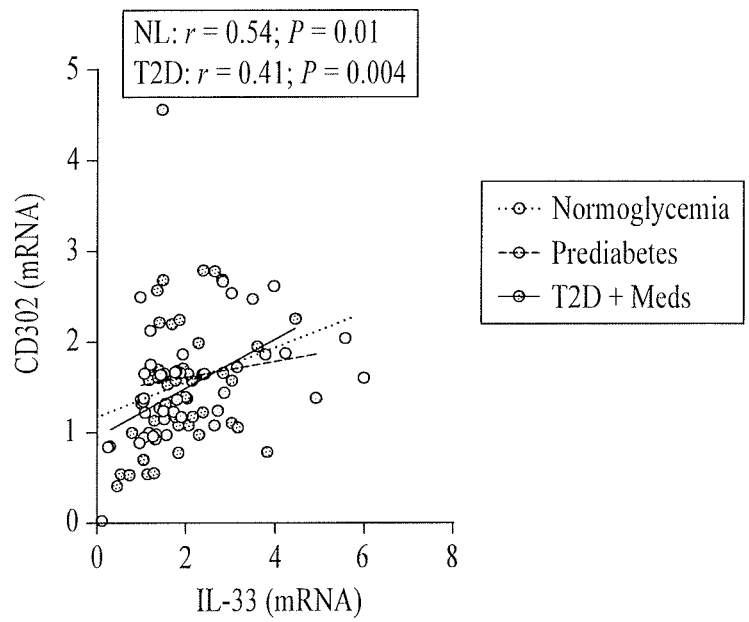
FIG. 4C depicts a scatter plot of the association between the adipose tissue IL-33 expression levels and CD302 expression levels in subjects having normoglycemia, prediabetes, and managed Type II diabetes.
Figure 4D:
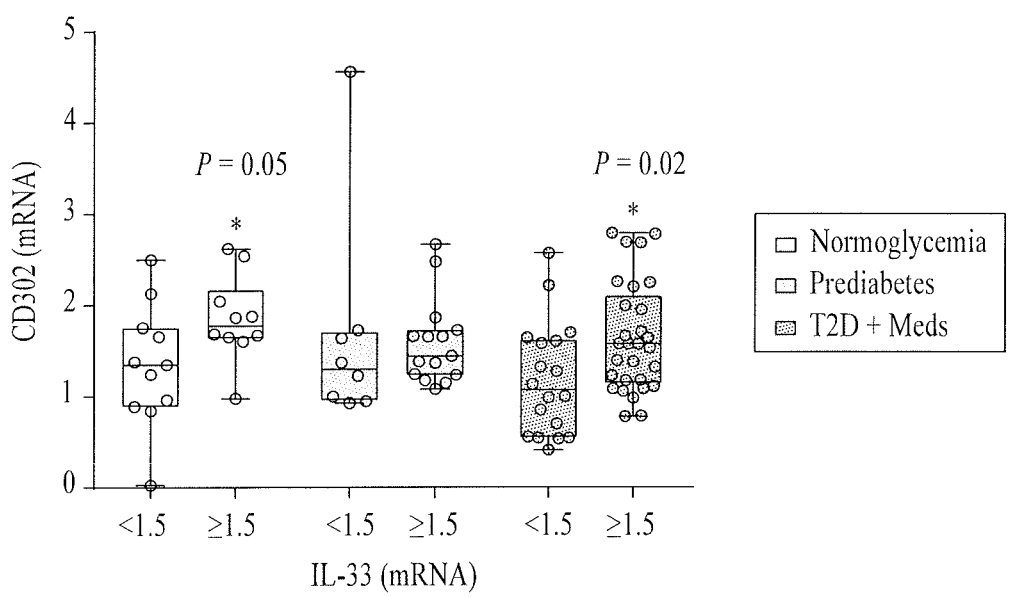
FIG. 4D depicts a box plot of the association between the adipose tissue IL-33 expression levels and CD302 expression levels in subjects having normoglycemia, prediabetes, and managed Type II Diabetes.
Figure 5A:
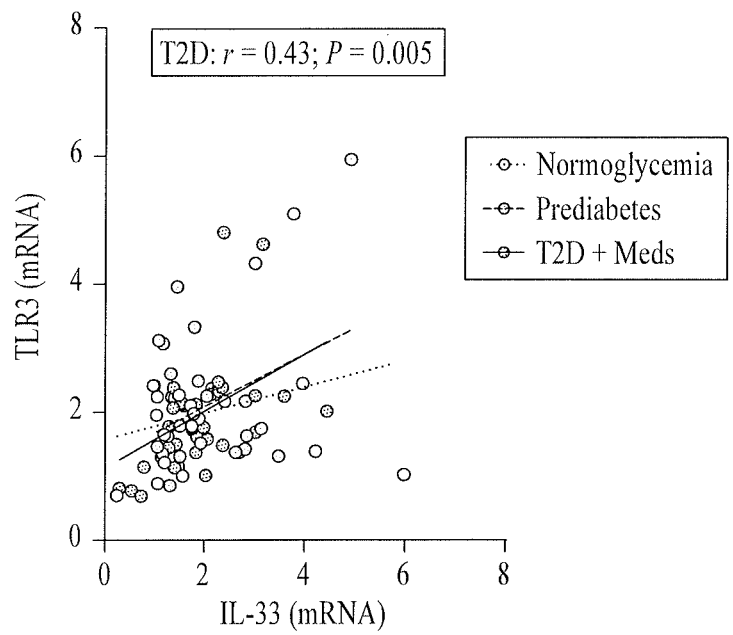
FIG. 5A depicts a scatter plot of the association between the adipose tissue IL-33 expression levels and TLR3 expression levels in subjects having normoglycemia, prediabetes, and managed Type II Diabetes.
Figure 5B:
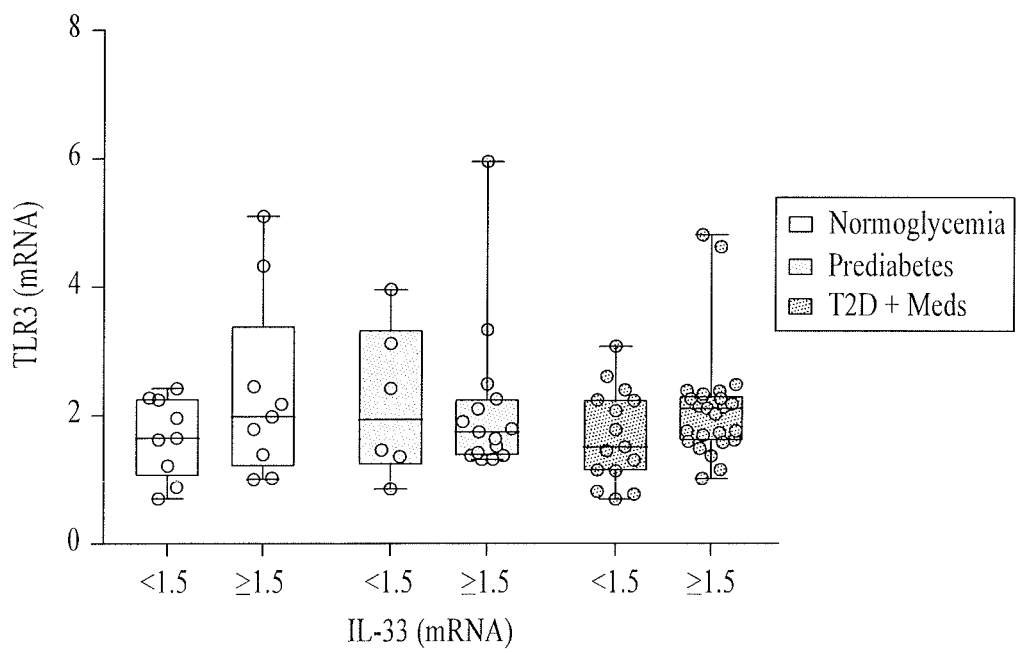
FIG. 5B depicts a box plot of the association between the adipose tissue IL-33 expression levels and TLR3 expression levels in subjects having normoglycemia, prediabetes, and managed Type II Diabetes.
Figure 5C:
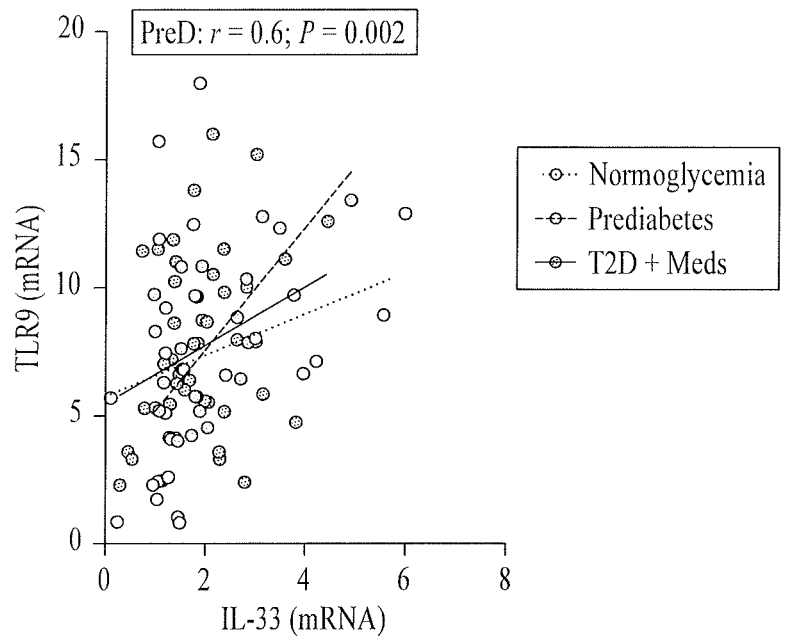
FIG. 5C depicts a scatter plot of the association between the adipose tissue IL-33 expression levels and TLR9 expression levels in subjects having normoglycemia, prediabetes, and managed Type II Diabetes.
Figure 5D:
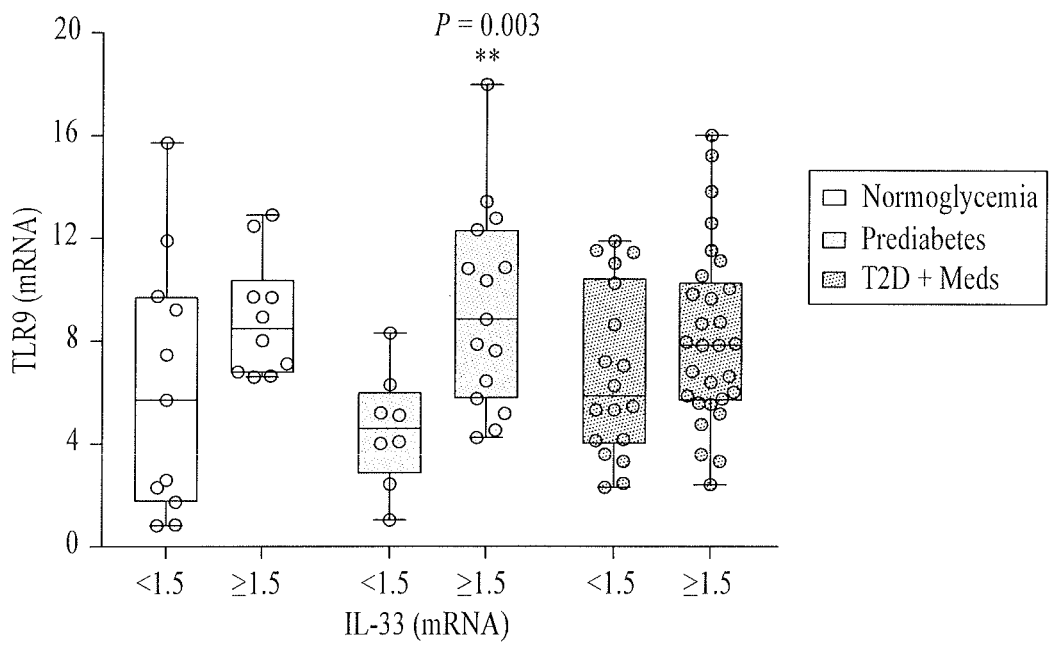
FIG. 5D depicts a box plot of the association between the adipose tissue IL-33 expression levels and TLR9 expression levels in subjects having normoglycemia, prediabetes, and managed Type II Diabetes.

Comparative analysis confirmed that higher levels of IL-33 tended to be associated with higher CD302 expression in individuals with normoglycemia (although this did no reach statistical significance, P=0.05; median 1.77, n=10 vs. median 1.3, n=11) and Type II Diabetes (P=0.02; median 1.57, n=29 vs. median 1.07, n=18) but not in those with prediabetes (see FIGS. 4C-4D). There was no association between IL-33 and CLEC7A among individuals with normoglycemia, prediabetes, or Type II Diabetes (data not shown). There was no correlation between IL-33 and toll-like receptor (TLR) 2, TLR4, TLR7, TLR8, and TLR10 among individuals with normoglycemia, prediabetes, or Type II Diabetes. However, IL-33 was directly correlated with TLR3 (r=0.43; P=0.005; n=40) in individuals with Type II Diabetes, although comparative analysis did not reach statistical significance (see FIGS. 5A-5B). Interestingly, IL-33 was directly correlated with TLR9 (r=0.6; P=0.002; n=23) in individuals with prediabetes; and comparative analysis confirmed that higher levels of IL-33 were associated with significantly higher TLR9 expression (P=0.003; median 8.84, n=15 vs. median 4.6, n=8) (see FIGS. 5C-5D).

9. Association Between Adipose Tissue IL-33 and Mediators of Inflammation and Immune Recognition.

Figure 6A:
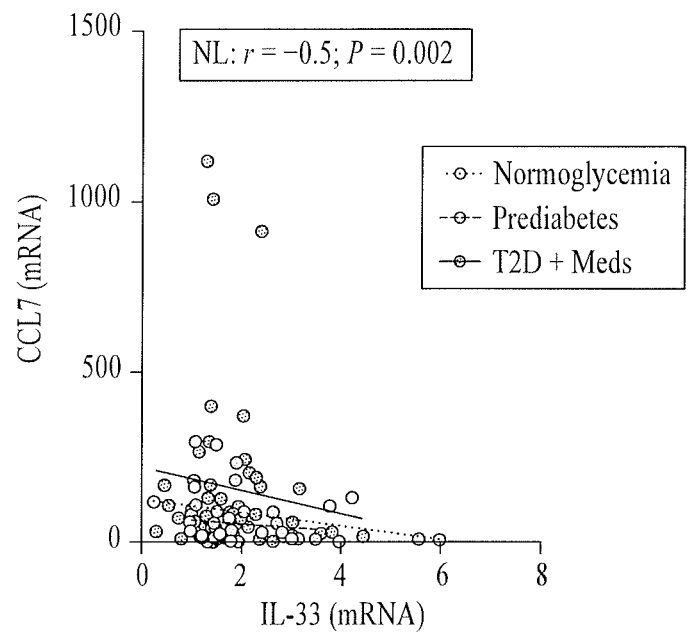
FIG. 6A depicts a scatter plot of the association between the adipose tissue IL-33 expression levels and CCL7 expression levels in subjects having normoglycemia, prediabetes, and managed Type II Diabetes.
Figure 6B:
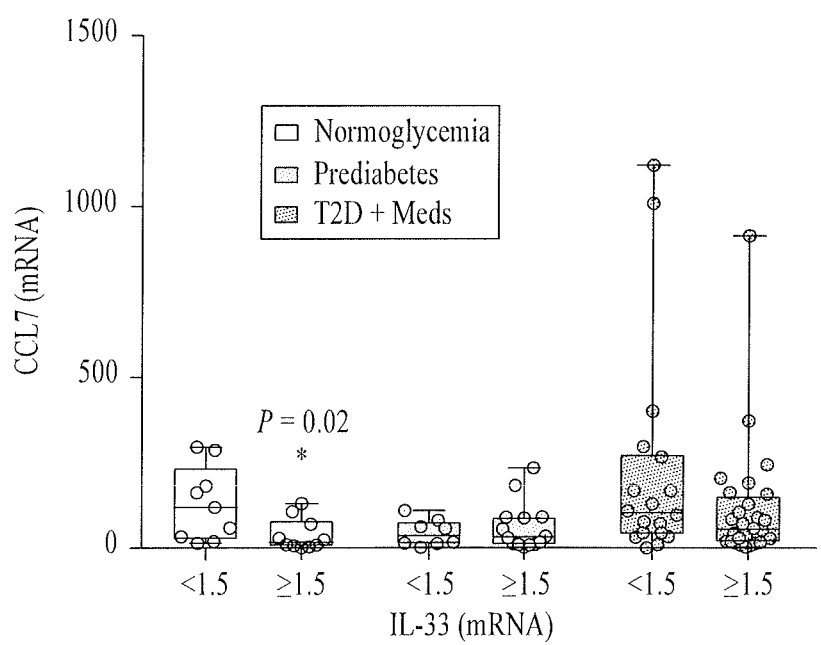
FIG. 6B depicts a box plot of the association between the adipose tissue IL-33 expression levels and CCL7 expression levels in subjects having normoglycemia, prediabetes, and managed Type II Diabetes.
Figure 6C:
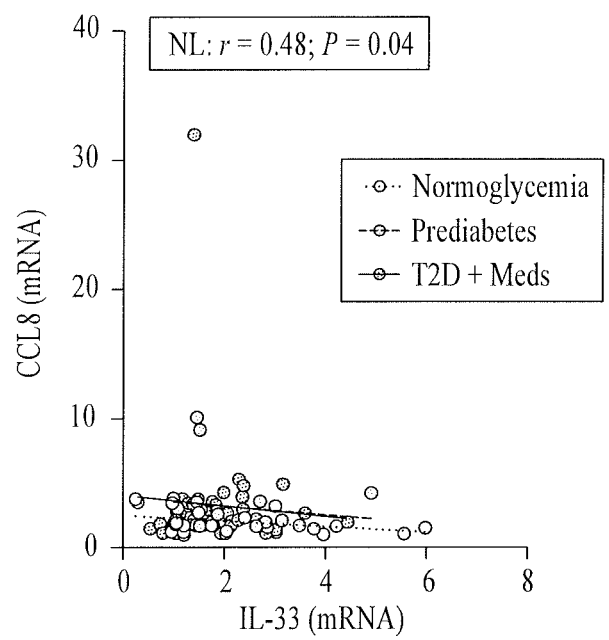
FIG. 6C depicts a scatter plot of the association between the adipose tissue IL-33 expression levels and CCL8 expression levels in subjects having normoglycemia, prediabetes, and managed Type II Diabetes.
Figure 6D:
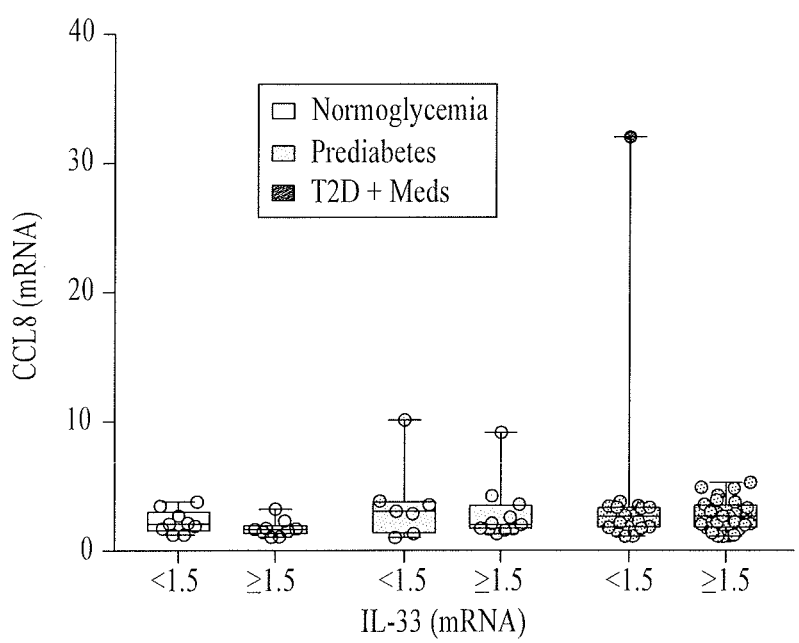
FIG. 6D depicts a box plot of the association between the adipose tissue IL-33 expression levels and CCL8 expression levels in subjects having normoglycemia, prediabetes, and managed Type II Diabetes.

The association between adipose tissue IL-33 and inflammatory cytokines and chemokines was evaluated in individuals with normoglycemia, prediabetes, and Type II Diabetes. There was no association between IL-33 and inflammatory cytokines including IL-1β, TNF-α, IL-8, IL-18, or IL-23A. Similarly, there was no association between IL-33 and chemokine (c-C motif) ligand (CCL) 2 (CCL2), CCLS, CCL11, CCL15, CCL19, CCL20, (C-X-C motif) ligand (CXCL) 8, CXCL9, and CXCL10, among individuals with normoglycemia (r=−0.5; P=0.02; n=19) but not in those with prediabetes or Type II Diabetes. Comparative analysis confirmed that higher levels of IL-33 were associated with significantly lower CCL7 in individuals with normoglycemia (P=0.02; median 16.7, n=10 vs. median 118.8, n=9) but not in those with prediabetes or Type II Diabetes (FIGS. 6A-6B). Similarly, IL-33 was inversely correlated with CCL8 in individuals with normoglycemia (r=−0.48; P=0.04; n=18) but not in those with prediabetes or Type II Diabetes. However, although higher levels of IL-33 were associated with lower CCL8 in individuals with normoglycemia, this did not reach statistical significance (see FIGS. 6C-6D).

Figure 7A:
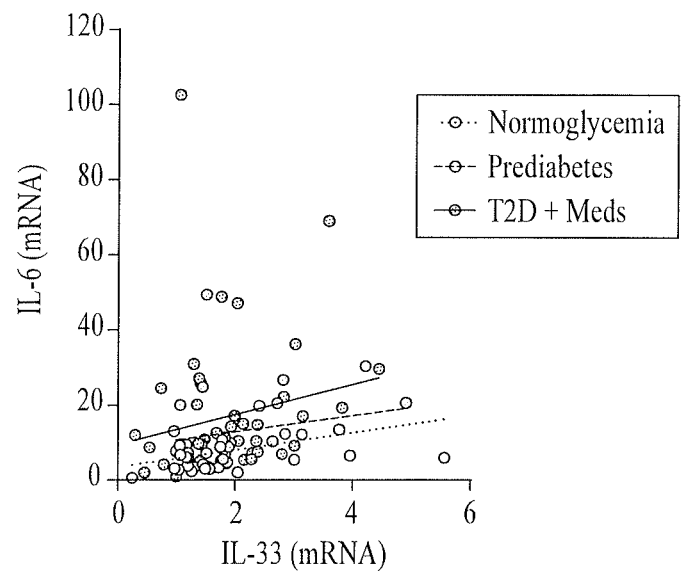
FIG. 7A depicts a scatter plot of the association between the adipose tissue IL-33 expression levels and IL-6 expression levels in subjects having normoglycemia, prediabetes, and managed Type II Diabetes.
Figure 7B:
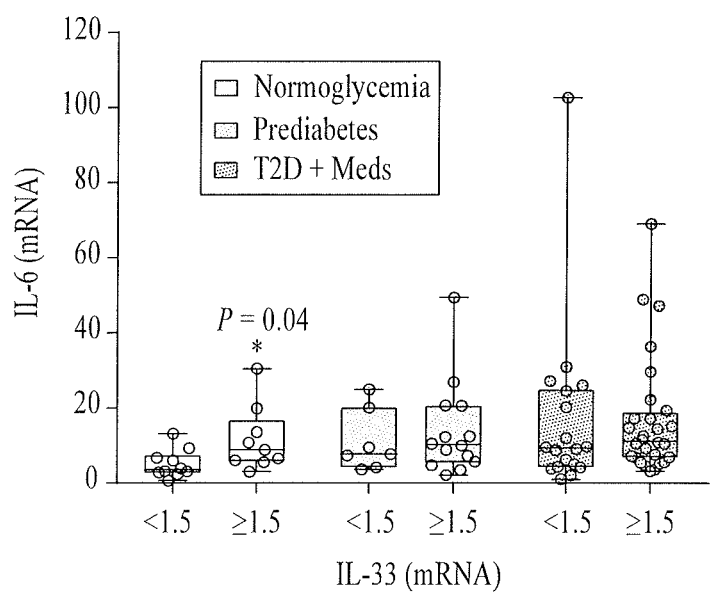
FIG. 7B depicts a box plot of the association between the adipose tissue IL-33 expression levels and IL-6 expression levels in subjects having normoglycemia, prediabetes, and managed Type II Diabetes.
Figure 7C:
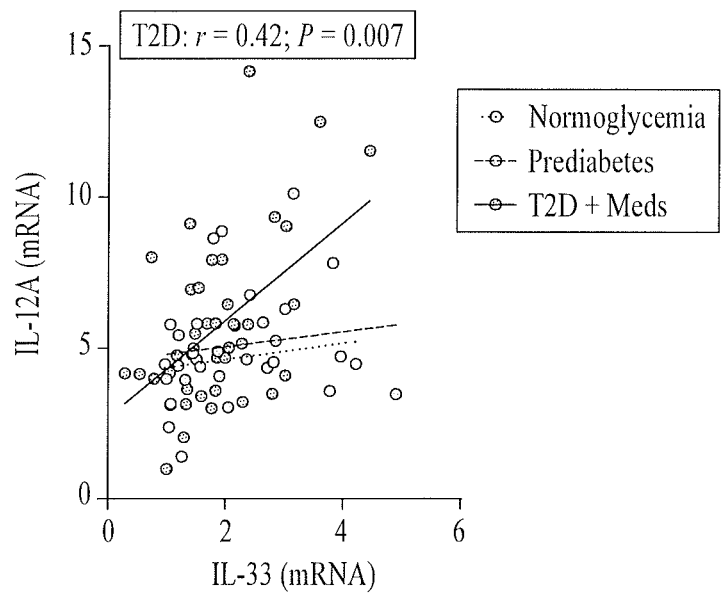
FIG. 7C depicts a scatter plot of the association between the adipose tissue IL-33 expression levels and IL-12A expression levels in subjects having normoglycemia, prediabetes, and managed Type II Diabetes.
Figure 7D:
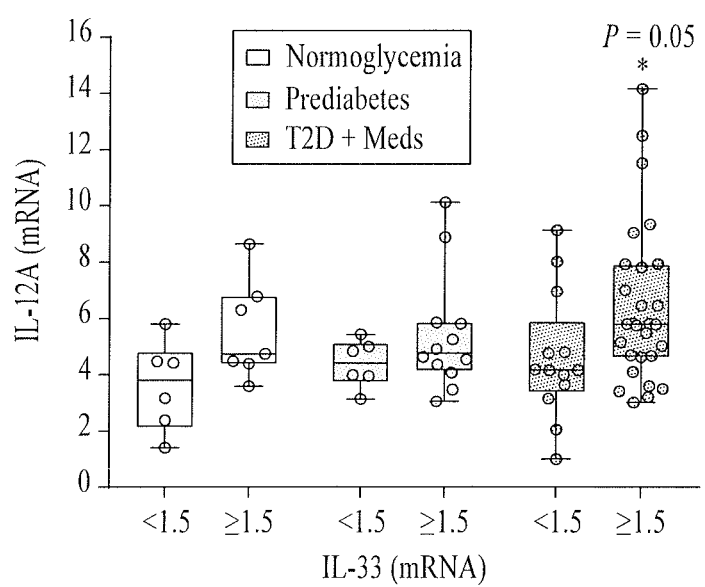
FIG. 7D depicts a box plot of the association between the adipose tissue IL-33 expression levels and IL-12A expression levels in subjects having normoglycemia, prediabetes, and managed Type II Diabetes.

Interestingly, although IL-33 was not correlated with IL-6 in individuals with normoglycemia, prediabetes, or Type II Diabetes, higher levels of IL-33 were associated with significantly higher IL-6 in individuals with normoglycemia (P=0.04; median 8.86, n=9 vs. median 3.5, n=10) but not in those with prediabetes or Type II Diabetes (see FIGS. 7A-7B). Furthermore, IL-33 was directly correlated with IL-12A (IL-12B was not tested) in individuals with Type H Diabetes (r=0.42; P=0.007; 11=41) but not in those with normoglycemia or prediabetes. Among individuals with Type II Diabetes, those who had higher levels of IL-33 has higher levels (although statistically nonsignificant) of IL-12A compared with those who had lower levels of IL-33 (P=0.05; median 5.79, n=28 vs. median 4.2, n=13) (see FIGS. 7C-7D).

Figure 8A:
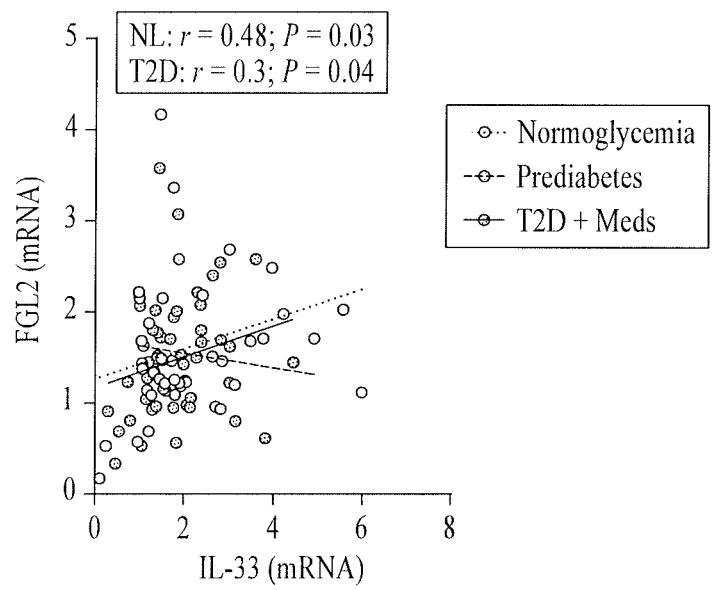
FIG. 8A: depicts a scatter plot of the association between the adipose tissue IL-33 expression levels and FGL2 expression levels in subjects having normoglycemia, prediabetes, and managed Type II Diabetes.
Figure 8B:
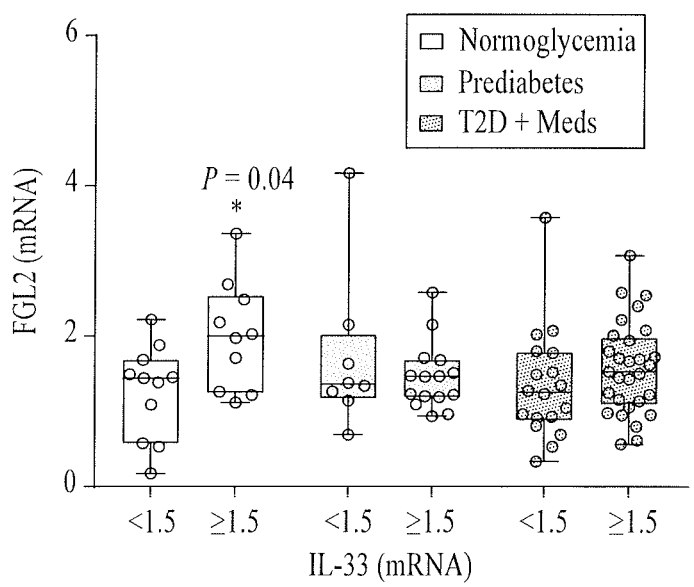
FIG. 8B: depicts a box plot of the association between the adipose tissue IL-33 expression levels and FGL2 expression levels in subjects having normoglycemia, prediabetes, and managed Type II Diabetes.

Next, whether adipose tissue IL-33 was associated with downstream Th2 cytokines and/or mediators of immune regulation was studied. There was no association between IL-33 and IL-5, IL-10, IL-13, TGB-β, FOXP3, or CD127. However, IL-33 was directly correlated with fibrinogen-like protein 2 (FGL2) in individuals with normoglycemia (r=0.48; P=0.03; n=21) and Type II Diabetes (r=0.3; P=0.04; n=47) but not in those with prediabetes. Among individuals with normoglycemia, those who had higher levels of IL-33 had significantly higher levels of FGL2 (P=0.04; median 2.0, n=10 vs. median 1.44, n=11) compared with those who had lower levels of IL-33 (FIGS. 8A-8B).

10. Association Between Adipose Tissue IL-33 and "Beiging" of Adipose Tissue.

Figure 9A:
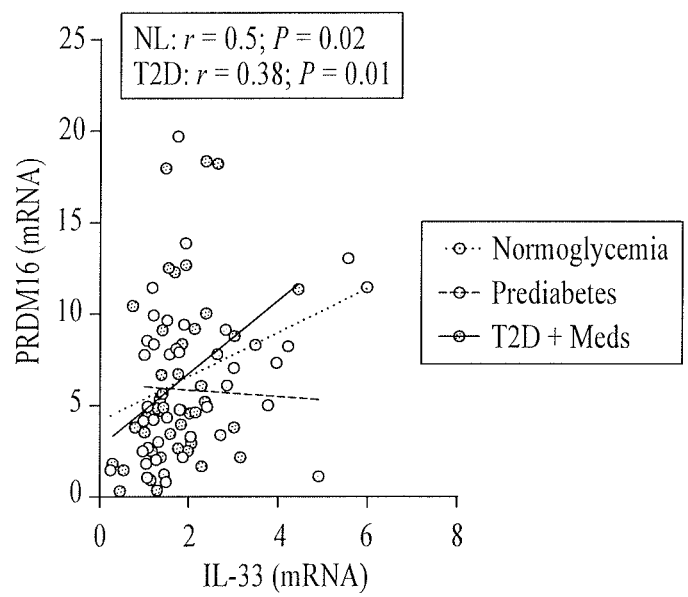
FIG. 9A: depicts a scatter plot of the association between the adipose tissue IL-33 expression levels and PRDM16 expression levels in subjects having normoglycemia, prediabetes, and managed Type II Diabetes.
Figure 9B:
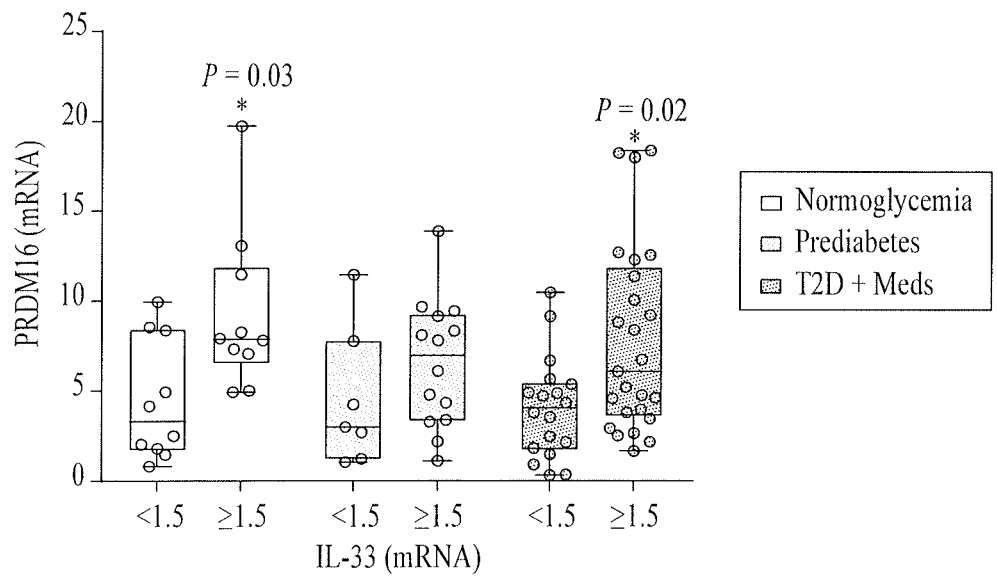
FIG. 9B: depicts a box plot of the association between the adipose tissue IL-33 expression levels and PRDM16 expression levels in subjects having normoglycemia, prediabetes, and managed Type II Diabetes.

Whether adipose tissue IL-33 was associated with genes involved in beiging of adipose tissue in individuals with normoglycemia, prediabetes, and Type II Diabetes was studied. Although IL-33 was not correlated with UCP1 or COX7A1, it was directly correlated with PR domain containing 16 (PRDM16) in individuals with normoglycemia (r=0.5; P=0.02; n=20) and Type H Diabetes (r=0.38; P=0.01; n=43) but not in those with prediabetes. Similarly, higher levels of IL-33 were associated with significantly higher PRDM16 in individuals with normoglycemia (P=0.03; median 7.9, n=10 vs. median 3.3, n=10) and Type II Diabetes (P=0.02; median 6.1, n=25 vs. median 4.1, n=18) but not in those with prediabetes (see FIGS. 9A-9B).

Further data collected in the course of conducting the experiments discussed in this example may be found in Table 2 (Kruskal-Wallis Test).

TABLE 2

Gene Expression P-Values

| Gene | Assay ID | Gene Expression Among Individuals with Varying Glycemia |
| --- | --- | --- |
| ST2 | Hs00545033_m1 | P ≥ 0.05 |
| Il-5 | Hs01548712_g1 | P ≥ 0.05 |
| IL-6 | Hs00985639_m1 | P = 0.047 |
| IL-8 | Hs00174103_m1 | P ≥ 0.05 |
| IL-10 | Hs00961622_m1 | P ≥ 0.05 |
| IL-12A | Hs01073447_m1 | P ≥ 0.05 |
| IL-13 | Hs00174379_m1 | P = 0.02 |
| IL-18 | Hs01038788_m1 | P ≥ 0.05 |
| IL-23A | Hs00900828_g1 | P ≥ 0.05 |
| IL-33 | Hs00369211_m1 | P ≥ 0.05 |
| IL-1β | Hs01555410_m1 | P ≥ 0.05 |
| TNF-α | Hs01113624_g1 | P ≥ 0.05 |
| TGF-β | Hs00820148_g1 | P ≥ 0.05 |
| FGL2 | Hs00173847_m1 | P ≥ 0.05 |
| PRDM16 | Hs00922674_m1 | P ≥ 0.05 |
| UCP1 | Hs00222453_m1 | P ≥ 0.05 |
| COX7A1 | Hs03045102_g1 | P ≥ 0.05 |
| FOXP3 | Hs01085834_m1 | P ≥ 0.05 |
| CD11c | Hs00174217_m1 | P ≥ 0.05 |
| CD68 | Hs02836816_m1 | P ≥ 0.05 |
| CD86 | Hs01567026_m1 | P ≥ 0.05 |
| CD127 | Hs00902334_m1 | P ≥ 0.05 |
| CD163 | Hs00174705_m1 | P ≥ 0.05 |
| CD302 | Hs00994886_m1 | P ≥ 0.05 |
| CLEC7A | Hs01902549_s1 | P ≥ 0.05 |
| TLR2 | Hs01872448_s1 | P ≥ 0.05 |
| TLR3 | Hs01551078_m1 | P ≥ 0.05 |
| TLR4 | Hs00152939_m1 | P ≥ 0.05 |
| TLR7 | Hs01933259_s1 | P ≥ 0.05 |
| TLR8 | Hs00152972_m1 | P ≥ 0.05 |
| TLR9 | Hs00370913_s1 | P ≥ 0.05 |
| TLR10 | Hs01935337_s1 | P ≥ 0.05 |
| CCL2 | Hs00234140_m1 | P = 0.03 |
| CCL5 | Hs00982282_m1 | P ≥ 0.05 |
| CCL7 | Hs00171147_m1 | P ≥ 0.05 |
| CCL8 | Hs04187715_m1 | P ≥ 0.05 |
| CCL11 | Hs00237013_m1 | P ≥ 0.05 |
| CCL15 | Hs00361122_m1 | P ≥ 0.05 |
| CCL19 | Hs00171149_m1 | P = 0.002 |
| CCL20 | Hs01011368_m1 | P ≥ 0.05 |
| CXCL9 | Hs00171065_m1 | P ≥ 0.05 |
| CXCL10 | Hs01124251_g1 | P = 0.025 |
| CCR1 | Hs00928897_s1 | P ≥ 0.05 |
| CCR2 | Hs00704702_s1 | P = 0.03 |
| CCR5 | Hs99999149_s1 | P = 0.016 |

It is to be understood that the method for preventing progression to Type II Diabetes is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for reducing the risk of progression from prediabetes to Type II Diabetes in a subject comprising:
   collecting a biological sample from the subject;
   detecting for the presence of a Type II Diabetes risk variant expression profile in the biological sample; and
   administering an intervention to the subject, to reduce the risk of the subject developing Type II Diabetes;
   wherein the subject is a human, the Type II Diabetes risk variant is a loss of direct correlation of IL-33 and ST2 expression; and wherein the intervention comprises administering metformin to the subject.

2. The method for reducing the risk of progression from prediabetes to Type II Diabetes of claim 1, wherein the Type II Diabetes risk variant expression profile is determined using RT-PCR.

3. The method for reducing the risk of progression from prediabetes to Type II Diabetes of claim 1, wherein the intervention further comprises prescribing regular exercise for the subject to reduce the subject's risk of developing Type II Diabetes.

4. The method for reducing the risk of progression from prediabetes to Type II Diabetes of claim 1, wherein the intervention further comprises prescribing a modified diet selected from the group consisting of one or more of restricted calorie, low fat, low carbohydrate, flexitarian, vegan, high fiber and raw food diets to reduce the subject's risk of developing Type II Diabetes.

5. The method for reducing the risk of progression from prediabetes to Type II Diabetes of claim 1, wherein the intervention further comprises administering at least one further pharmaceutical to the subject, wherein the pharmaceutical is selected from the group consisting of atorvastatin, fluvastatin, lovastatin, pitavastatin, pravastatin, rosuvastatin calcium, simvastatin, sulfonylureas, meglitinides, thiazolinediones, DPP-4 inhibitors, GLP-1 receptor agonists, SGLT2 inhibitors, insulin, diuretics, beta-blockers, ACE inhibitors, angiotensin II receptor blockers, calcium channel blockers, alpha blockers, alpha-2 receptor agonists, non-steroidal anti-inflammatory drugs, pharmaceutical grade probiotics, and combinations thereof.

6. The method for reducing the risk of progression from prediabetes to Type II Diabetes of claim 4, wherein the intervention further comprises administering a dietary supplement to the subject to reduce the subject's risk of developing Type II Diabetes, and wherein the dietary supplement is selected from the group consisting of a probiotic, a prebiotic, a synbiotic, and a combination thereof.

7. The method for reducing the risk of progression from prediabetes to Type II Diabetes of claim 1, wherein the intervention further comprises administering a dietary supplement to the subject to reduce the subject's risk of developing Type II Diabetes, and wherein the dietary supplement is selected from the group consisting of a probiotic, a prebiotic, a synbiotic, and a combination thereof.

8. The method for reducing the risk of progression from prediabetes to Type II Diabetes of claim 1, wherein the biological sample comprises adipose tissue.

9. The method for reducing the risk of progression from prediabetes to Type II Diabetes of claim 1, wherein the biological sample comprises one or more of PBMCs, blood serum, and plasma.

* * * * *